United States Patent [19]

Matson

[11] Patent Number: 4,567,143
[45] Date of Patent: Jan. 28, 1986

[54] PROCESS FOR PREPARING 4'-DESCHLOROREBECCAMYCIN

[75] Inventor: James A. Matson, Fayetteville, N.Y.

[73] Assignee: Bristol-Myers Company, New York, N.Y.

[21] Appl. No.: 690,271

[22] Filed: Mar. 18, 1985

Related U.S. Application Data

[62] Division of Ser. No. 646,673, Sep. 4, 1984, Pat. No. 4,524,145.

[51] Int. Cl.$^4$ .................. C12P 17/18; C12R 1/365
[52] U.S. Cl. .................................. 435/119; 435/872
[58] Field of Search ............... 435/119, 872; 424/180; 536/22, 24; 514/43

[56] References Cited

U.S. PATENT DOCUMENTS 4,524,145  6/1985  Matson ........................... 514/43

FOREIGN PATENT DOCUMENTS 0115350  8/1984  European Pat. Off. ............ 435/119

OTHER PUBLICATIONS

*J. Antibiotics* 30 (4), A New Alkaloid AM-2282 of Steptomyces Origin Taxonomy, Fermentation, Isolation and Preliminary Characterization, S. Omura et. al., pp. 275–282, 1977.

*J. C. S. Chem. Comm.*, X-Ray Crystal Structure of Staurosporing: a New Alkaloid from a Streptomyces Strain, A. Furusaki et. al., pp. 800–801, 1978.

*Angew. Chem. Int. Ed. Engl.* 19(6), Indole Pigments from the Fruiting Bodies of the Slime Mold *Arcyria denudata*, W. Steglich et. al., pp. 459–460, 1980.

*Primary Examiner*—Alvin E. Tanenholtz
*Assistant Examiner*—Elizabeth C. Weimar
*Attorney, Agent, or Firm*—David M. Morse

[57] ABSTRACT

A new antitumor antibiotic designated herein as 4'-deschlororebeccamycin is produced by fermentation of *Nocardia aerocolonigenes* ATCC 39243. The new compound possesses antibacterial activity and inhibits the growth of tumors in experimental animals.

1 Claim, No Drawings

4,567,143

PROCESS FOR PREPARING 4'-DESCHLOROREBECCAMYCIN

CROSS-REFERENCE TO RELATED APPLICATIONS

This application is a division of co-pending application Ser. No. 646,673 filed Sept. 4, 1984 now U.S. Pat. No. 4,524,145.

BACKGROUND OF THE INVENTION

1. Field of the Invention

This invention relates to a novel antitumor antibiotic and to its production and recovery.

2. Description of the Prior Art

The novel compound of the present invention is related in structure to the antitumor agent, rebeccamycin, disclosed and claimed in co-pending application Ser. No. 461,817 filed Jan. 28, 1983, now U.S. Pat. No. 4,487,925 the entire disclosure of which is hereby incorporated by reference. Rebeccamycin has the formula

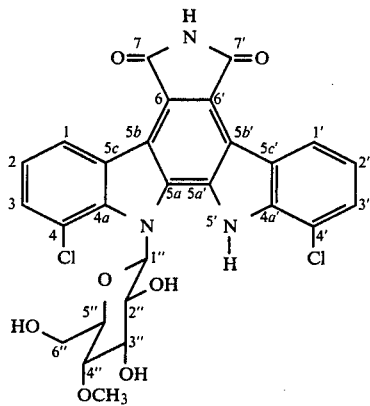

and is obtained by cultivating Nocardia aerocolonigenes.

Somewhat related in structure to the compound of the present invention is the antitumor agent, staurosporine (also called AM-2282), obtained from fermentation of Streptomyces staurosporeus. Staurosporine is described in J.C.S. Chem. Comm., 1978, Pg. 800–801 and in J. Antibiotics 30(4): 275-282 (1977).

Agnew Chem. Int. Ed. Engl. 19(6): 459–460 (1980) discloses several indole pigments obtained from the fruiting bodies of the slime mold Arcyria denudata which are structurally related to staurosporine. Certain of the pigments exhibit activity against Bacillus brevis and B. subtilis.

SUMMARY OF THE INVENTION

This invention relates to a new antitumor antibiotic designated herein as 4'-deschlororebeccamycin having the structural formula

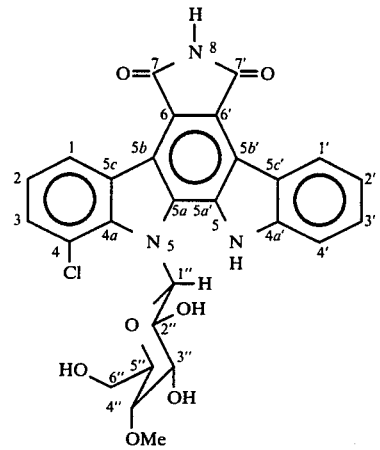

and to the process for the preparation, isolation and purification of 4'-deschlororebeccamycin in substantially pure form.

The antibiotic of the present invention is obtained by fermentation of a 4'-deschlororebeccamycin-producing strain of Nocardia aerocolonigenes, preferably Nocardia aerocolonigenes strain C38,383-RK2 (ATCC 39243) or a mutant thereof, in an aqueous nutrient medium under submerged aerobic conditions until a substantial amount of 4'-deschlororebeccamycin is produced by said microorganism in said culture medium and, optionally, recovering the 4'-deschlororebeccamycin from the culture medium substantially free of co-produced substances.

The compound 4'-deschlororebeccamycin exhibits antimicrobial activity and also activity against experimental animal tumor systems, e.g. P-388 leukemia in mice.

DETAILED DESCRIPTION

The 4'-deschlororebeccamycin of the present invention is produced by fermentation of a 4'-deschlororebeccamycin-producing strain of Nocardia aerocolonigenes.

An especially preferred 4'-deschlororebeccamycin-producing strain is that disclosed in U.S. application Ser. No. 461,817 filed Jan. 28, 1983 now U.S. Pat. No. 4,487,925 as being the producing organism for rebeccamycin. The present applicant has discovered that during cultivation of this microorganism there is co-produced along with rebeccamycin the 4'-deschlororebeccamycin product of the present invention. This preferred producing microorganism, designated C38,383-RK2, was isolated from a soil sample collected in Panama. Cultures of this strain have been deposited in the American Type Culture Collection, Rockville, Md., and added to their permanent collection of microorganisms as ATCC 39243.

The results of taxonomic studies performed on strain C38,383-RK2 indicate that the strain is classified as an atypical species of the genus Nocardia. Based on the characteristics indicated below, strain C38,383-RK2 is believed to belong to the species group of Nocardia aerocolonigenes.

Strain C38,383-RK2 has the following properties:

Morphology

Strain C38,383-RK2 forms unicellular filamentous cells which develop into substrate and aerial mycelia. Both mycelia are long, well branched and not fragmented into short filaments (0.5 μm in width). Arthrospores are born in the whole of aerial mycelium. These spores are arranged with intercalation of empty hyphae, or formed as a continuous chain. Like the sporulation of *Nocardiopsis dassonvillei*, (*Intl. J. Syst. Bacteriol.* 26: 487–493, 1976) the aerial hyphae of strain C38,383 are divided into long segments which subsequently subdivide into spores of irregular size. The chains of intercalary or continuous spores are straight or flexuous in shape. Extremely long spore-chains which contain 50 to 100 spores in a chain are formed along with short or moderate length of chains. The spores are cylindrical in shape, 0.5~0.7×0.7~5 μm in size, and have a smooth surface.

Sclerotia are formed on the aerial mycelium, but sporangia, motile spores and whorls are not observed.

Cultural Characteristics

Strain C38,383 is an obligately aerobic actinomycete, and grows well in most agar media. The aerial mycelium is formed abundantly on Czapek's sucrose-nitrate agar, ISP Medium Nos. 2,4,5 and 7, nutrient agar and Bennett's agar, but poorly on glucose-asparagine agar and ISP Medium Nos. 3 and 6. The color of aerial mycelium is white, yellowish white or pale yellow. A yellowish pigment is formed in the substrate mycelium, which diffuses slightly into agar medium. This pigment is not a pH-indicator. Melanoid pigment is not produced. The cultural characteristics are shown in Table 1.

Physiological Characteristics

The optimal growth temperature for strain C38,383 ranges from 28° C. to 37° C., and moderate growth is seen at 20° C. and 41° C. No growth is observed at 7° C. and 45° C. Gelatin and starch are decomposed. Tyrosinase reaction is negative. The growth is inhibited in the presence of 8% NaCl, but not by lysozyme at 0.01%. Strain C38,383 utilizes most sugars for growth. The physiological characteristics and utilization of carbohydrates are shown in Tables 2 and 3, respectively.

Cell Wall Amino Acid and Whole Cell Sugar Components

The amino acid composition in the cell wall was examined according to the methods described by Becker et al. (*Appl. Microbial.* 13: 236–243, 1965) and Yamaguchi (*J. Bacteriol.* 89: 441–453, 1965), and the sugar component in the whole cell hydrolyzate was identified according to the procedures outlined by Lechevalier and Lechevalier in *Biology of the Actinomycetes and Related Organisms* 11: 78–92, 1976. The cell wall of strain C38,383 contains meso-diaminopimelic acid but lacks glycine. Whole cell hydrolyzate shows the presence of glucose, galactose, mannose and rhamnose. The above-mentioned cell wall composition and whole cell sugar components indicate that the strain C38,383 is an actinomycete species of cell wall type IIIC.

Taxonomy

Strain C38,383 was compared with eight genera of order Actinomycetales, including Nocardia, Micropolyspora, Microtetraspora, Nocardiopsis, Saccharopolyspora, Pseudonocardia, Actinomadura and Streptoalloteichus, all of which produce spore-chains on the aerial mycelium and contain mesodiaminopimelic acid in the cell wall. Among these eight genera, the genus Nocardiopsis is most related to strain C38,383 in the spore-chain and spore morphology, but differs from strain C38,383 in the absence of galactose and mannose in the whole cell hydrolyzate.

Gordon et al. (*J. Gen. Microbiol.* 109: 69–78, 1978) characterized 14 taxa of nocardiae based on the physiological properties and the chemical composition in whole cell hydrolyzate. Strain C38,383 was most similar to *Nocardia aerocolonigenes* in the amino acid and sugar composition in whole cell hydrolyzate. Therefore, strain C38,383 was compared with the diagnostic physiological properties of *N. aerocolonigenes*. As shown in Table 4, strain C38,383 was found to be closely related to *N. aerocolonigenes* but significantly different from *Nocardia* (*Nocardiopsis*) *dassonvillei*. However, all 14 strains of *N. aerocolonigenes* lack or lose the abilities to form spores and aerial mycelium. Thus, strain C38,383 is considered to be a sporogenic species in the taxon of *Nocardia aerocolonigenes*.

Strain C38,383 was also found to lose its ability to form aerial mycelium and spores. After five successive transfers, 70% of single isolates lost these abilities. Such property of strain C38,383 seems to be similar to the reported variation of *Nocardia aerocolonigenes* in the formation of spores and aerial mycelium.

TABLE 1

| Cultural Characteristics of Strain No. C38,383* | | |
|---|---|---|
| Tryptone-yeast extract broth (ISP No. 1) | G** | moderate; floccose, pale yellow pellets |
| | D | none |
| Sucrose-nitrate agar (Czapek's agar) | G | abundant |
| | R | strong yellow (84)*** to vivid yellow (82) |
| | A | moderate, yellowish white (92) to pale yellow (89) |
| | D | dark grayish yellow (91) to light olive brown (94) |
| Glucose-asparagine agar | G | poor |
| | R | white (263) |
| | A | scant, yellowish white (92) to pale yellow (89) |
| | D | none |
| Glycerol-asparagine agar (ISP No. 5) | G | abundant |
| | R | brilliant yellow (83) to strong yellow (84) |
| | A | abundant, pale yellow (89) to light yellow (86) |
| | D | yellow gray (93) to grayish yellow (90) |
| Inorganic salts-starch agar (ISP No. 4) | G | abundant |
| | R | pale yellow (89) to strong yellow (84) |
| | A | abundant, white (263) to yellowish white (92) |
| | D | none |
| Tyrosine agar (ISP No. 7) | G | abundant |
| | R | brilliant yellow (83) to strong yellow (84) |
| | A | moderate, pale yellow (89) to light yellow (86) |
| | D | pale yellow (89) |
| Nutrient agar | G | abundant |
| | R | yellowish white (92) to pale yellow (89) |
| | A | abundant, white (263) |
| | D | none |
| Yeast extract-malt extract agar (ISP No. 2) | G | abundant |
| | R | brilliant orange yellow (67) to strong orange yellow (68) |
| | A | abundant, yellowish white (92) to pale yellow (89) |
| | D | dark orange yellow (72) to moderate yellowish brown (77) |
| Oat meal agar (ISP No. 3) | G | moderate |
| | R | light yellow (86) to brilliant yellow (83) |

TABLE 1-continued

Cultural Characteristics of Strain No. C38,383*

| | | |
|---|---|---|
| | A | scant, yellowish white (92) to pale yellow (89) |
| | D | none |
| Bennett's agar | G | abundant |
| | R | brilliant yellow (83) to strong yellow (84) |
| | A | abundant, yellowish white (92) pale yellow |
| | D | vivid yellow (82) |
| Peptone-yeast extract-iron agar (ISP No. 6) | G | moderate |
| | R | pale yellow (89) to light yellow (86) |
| | A | poor, white (263) to yellowish white (92) |
| | D | none |

*observed after incubation at 28° C. for 3 weeks
**Abbreviation: G = growth; R = reverse color; A = aerial mycelium; D = diffusible pigment
***Color and number in parenthesis follow the color standard in Kelly, K. L. & D. B. Judd: ISCC-NBS color-name charts illustrated with Centroid Colors. US Dept. of Comm. Cir. 553, Washington, D.C., No., 1975".

TABLE 2

Physiological Characteristics of Strain No. C38,383

| Test | Response | Method or Medium used |
|---|---|---|
| Range of temperature for growth | Maximal growth at 28° C. to 37° C. Moderate growth at 20° C. and 41° C. No growth at 7° C. and 45° C. | Bennett's agar |
| Gelatin liquefaction | Liquefied | 1% malt extract, 0.4% yeast extract, 0.4% glucose, 20% gelatin. |
| Starch hydrolysis | Hydrolyzed | Starch agar plate |
| Reactions in skimmed milk | Not coagulated and completely peptonized | Difco skimmed milk |
| Formation of melanoid pigment | negative | Tyrosine agar, peptone-yeast extract-iron agar, and tryptone-yeast extract broth |
| Tyrosinase reaction | Negative | Arai's method* |
| Nitrate reduction | Positive | Czapek's sucrose-nitrate broth |
| | Positive | 0.5% yeast extract, 1% glucose, 0.5% KNO$_3$, 0.1% CaCO$_3$. |
| Acid tolerance | Growth at pH 5.0. No growth at pH 4.5. | Yeast extract-malt extract agar |
| NaCl tolerance | Growth at 7% NaCl or less. No growth at 8% NaCl. | Basal medium: 1% yeast extract, 2% soluble starch, 1.5% agar. |
| Lysozyme tolerance | Tolerant. Growth at 0.01% lysozyme. | Trypticase soy broth plus 1.5% agar. |

*Arai, T. and Y. Mikami: Chromogenicity of Streptomyces. Appl. Microbiol. 23: 402–406, 1972.

TABLE 3

Carbohydrate Utilization of Strain No. C38,383

| | |
|---|---|
| Glycerol | + |
| D(−)-Arabinose | + |
| L(+)-Arabinose | + |
| D-Xylose | + |
| D-Ribose | + |
| L-Rhamnose | + |
| D-Glucose | + |
| D-Galactose | + |
| D-Fructose | + |
| D-Mannose | + |
| L(−)-Sorbose | − |
| Sucrose | + |
| Lactose | + |
| Melibiose | + |
| Trehalose | + |
| Raffinose | + |
| D(+)-Melezitose | − |
| Soluble starch | + |
| Cellulose | + |
| Dulcitol | − |
| Inositol | + |
| D-Mannitol | + |
| D-Sorbitol | − |
| Salicin | + | observed after incubation at 37° C. for 3 weeks
Basal medium: Pridham-Gottlieb's inorganic medium
Abbreviation: +: positive utilization, −: negative utilization

TABLE 4

Comparison of diagnostic physiological properties among strain C38,383, Nocardia aerocolonigenes and Nocardiopsis dassonvillei

| | Strain C38,383 | Nocardia* aerocolonigenes (14)** | Nocardiopsis* dassonvillei (31)** |
|---|---|---|---|
| Decomposition of: | | | |
| Adenine | − | − | + |
| Casein | + | + | + |
| Hypoxanthine | + | + | + |
| Tyrosine | + | + | + |
| Urea | − | + | − |
| Xanthine | − | − | + |
| Resistance to: | | | |
| Lysozyme | + | + | − |
| Rifampin | − | − | − |
| Hydrolysis of: | | | |
| Aesculin | + | + | − |
| Hippurate | − | V | + |
| Starch | + | + | + |
| Acid from: | | | |
| Inositol | + | + | − |
| Lactose | + | + | − |
| Melibiose | + | + | − |
| Raffinose | + | V | − |
| Utilization of: | | | |
| Benzoate | − | − | − |
| Citrate | + | + | + |
| Mucate | − | − | − |
| Succinate | + | + | + |
| Tartrate | − | − | − |
| Nitrite from nitrate | + | V | + |
| Survival at 50° C., 8 h | − | V | + |

+: positive, −: negative, V: 15 to 84% of the strains positive
*Data of Gordon et al. (J. Gen. Microbiol. 109:69–78, 1978)
**No. of strains examined It is to be understood that the present invention is not limited to use of the particular preferred strain C38,383-RK2 described above or to organisms fully answering the above descriptions. It is especially intended to include other 4'-deschlororebeccamycin-producing strains or mutants of the said organism which can be produced by conventional means such as x-radiation, ultraviolet radiation, treatment with nitrogen mustards, phage exposure, and the like.

Preparation of 4'-Deschlororebeccamycin

4'-Deschlororebeccamycin may be produced by cultivating a 4'-deschlororebeccamycin-producing strain of Nocardia aerocolonigenes, preferably a strain having the characteristics of Nocardia aerocolonigenes strain C38,383-RK2 (ATCC 39243) or a mutant thereof, under submerged aerobic conditions in an aqueous nutrient medium. The organism is grown in a nutrient medium containing an assimilable carbon source, for example, sucrose, lactose, glucose, rhamnose, fructose, mannose, melibiose, glycerol or soluble starch. The nutrient medium should also contain an assimilable nitrogen source such as fish meal, peptone, soybean flour, peanut meal, cottonseed meal or corn steep liquor. Nutrient inorganic salts can also be incorporated in the medium. Such salts may comprise any of the usual salts capable of providing sodium, potassium, ammonium, calcium, phosphate, sulfate, chloride, bromide, nitrate, carbonate or like ions.

Production of 4'-deschlororebeccamycin can be effected at any temperature conducive to satisfactory growth of the organism, e.g. 20°–41° C., and is conveniently carried out at a temperature of about 27° C.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of 4'-deschlororebeccamycin. The medium in which the vegetative inoculum is produced can be the same as, or different from, that utilized in the tank as long as it is such that a good growth of the producing organism is obtained.

In general, optimum production of 4'-deschlororebeccamycin is achieved after incubation periods of about seven days.

4'-Deschlororebeccamycin is a minor product of the fermentation and may be recovered from the culture medium and isolated in a substantially pure form according to the multistep procedure described in Example 1 below. Thus, the desired 4'-deschlororebeccamycin is found primarily in the mycelium and recovery from the mycelium may be effected by extraction with an organic solvent such as tetrahydrofuran. After reduction of the extract volume a crude solid containing the desired 4'-deschlororebeccamycin may be obtained. This crude solid may then be subjected to a multistep purification scheme illustrated in the following flow chart:

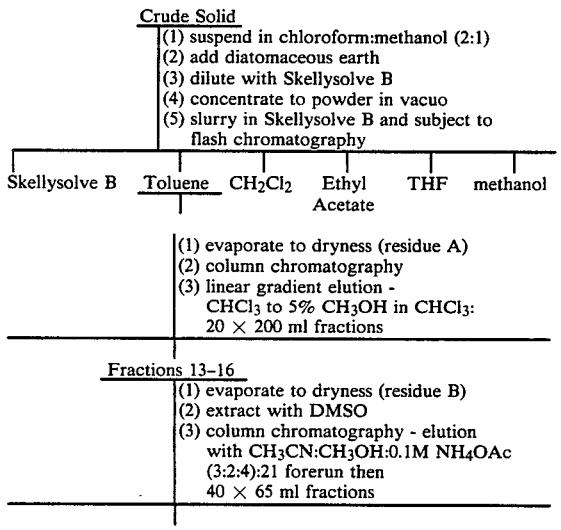

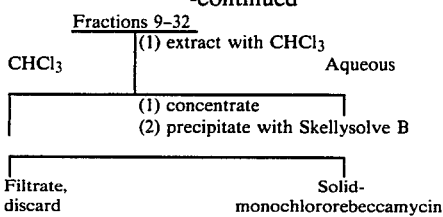

Physicochemical Properties of 4'-Deschlororebeccamycin

The physicochemical properties of 4'-deschlororebeccamycin are as follows:

4'-Deschlororebeccamycin is a yellow amorphous solid having a molecular formula of $C_{27}H_{22}O_7N_3Cl$ and a molecular weight of 535.8397. It is composed of the elements carbon, hydrogen, oxygen, nitrogen and chlorine. Elemental analysis data is as follows:

Calc'd for $C_{27}H_{22}O_7N_3Cl \cdot H_2O$: C, 58.54; H, 4.37; N, 7.58. Found: C, 58.43; H, 4.29; N, 7.29.

The high resolution mass spectrum of 4'-deschlororebeccamycin was determined with a Kratos MS-50 spectrometer and FAB ionization. The observed mass is as follows:

Calc'd for $(M+H)^+$ ion: 536.1224. Found for $(M+H)^+$ ion: 536.1188.

4'-Deschlororebeccamycin is insoluble in water and soluble in dimethylsulfoxide.

The infrared absorption spectrum of 4'-deschlororebeccamycin when pelleted in KBr exhibits characteristic bands at the following frequencies exhibited in reciprocal centimeters: 3400, 3330, 2930, 1745, 1703, 1575, 1490, 1470, 1458, 1435, 1398, 1380, 1330, 1273, 1238, 1140, 1105, 1083, 1050, 1015, 947, 910, 800, 798, 755, 738, 670, 665, 633.

The ultraviolet absorption spectrum of 4'-deschlororebeccamycin was determined in methanol (0.03462 g/l) under neutral conditions. Observed absorption maxima and absorptivities are as follows: 400 nm (8.6), 315 nm (96.5), 290 nm (107.7), 257 nm (sh), 235 nm (76.3).

A proton magnetic resonance spectrum of 4'-deschlororebeccamycin dissolved in dimethylsulfoxide was determined with a Bruker WM-360 spectrometer operating at 360 MHz and using tetramethylsilane as the internal standard. The observed chemical shifts (δ values), coupling constants (J values in Hz) and pattern descriptions are as follows: 11.81 (s, 1H, N8—H), 11.24 (s, 1H, N5'—H), 9.26 (d, J=7.9, 1H, Cl—H or Cl'—H), 9.10 (d, J=7.9, 1H, Cl—H or Cl'—H) 7.77 (d, J=7.9, 1H, C4'—H), 7.63 (m, 2H, C3—H and C3'—H), 7.42 (m, 2H, C2—H and C2'—H), 6.91 (d, J=9.4, 1H, C1"—H), 6.30 (bs, 1H, C6"—OH), 5.25 (d, J=5.7, 1H, C3"—OH), 4.91 (d, J=5.7, 1H, C2"—OH), 4.01 (bs, 2H, C6"—H), 3.90 (d, 1H, C5"—H), 3.67 (t, 1H, C4"—H), 3.62 (s, 3H, C4"—OCH3), 3.53 (m, 1H, C2"—H overlaps with H2O).

A carbon-13 magnetic resonance spectrum of 4'-deschlororebeccamycin dissolved in dimethylsulfoxide was determined with a Bruker WM-360 spectrometer operating at 22.5 MHz and using tetramethylsilane as the internal standard. The observed chemical shifts (ppm values) and assignments are as follows:

| Chemical Shift (ppm) | Assignment |
| --- | --- |
| 170.7 | C7 |
| 170.6 | C7' |
| 140.7 | C4a |
| 138.1 | C4a' |
| 130.4 | C5a |
| 129.9 | C5a' |
| 129.4 | C3' |
| 127.3 | C3 |
| 125.6 | C5c |
| 124.6 | C1' |
| 123.9 | C1 |
| 122.8 | C5c' |
| 122.3 | C2 |
| 121.1 | C6 |
| 120.6 | C2' |
| 119.4 | C6' |
| 119.1 | C5b' |
| 117.4 | C5b |
| 116.4 | C4 |
| 112.1 | C4' |
| 83.9 | C1" |
| 77.6 | C3" |
| 77.0 | C4" |
| 76.6 | C5" |
| 72.1 | C2" |
| 60.0 | $OCH_3$ |
| 58.7 | C6" |

Biological Activity of 4'-Deschlororebeccamycin

The antibacterial activity of 4'-deschlororebeccamycin was determined against a number of gram-positive and gram-negative organisms by the serial two-fold agar dilution method. The results are shown in Table 5 below in comparison with the activity of rebeccamycin.

TABLE 5

Antibacterial Activity of 4'-Deschlororebeccamycin

| | | Minimum Inhibitory Concentration (MIC) (mcg/ml) | |
| --- | --- | --- | --- |
| Organism | | Rebeccamycin | 4'-Deschlororebeccamycin |
| S. pneumoniae | A9585 | >125 | 32 |
| S. pyogenes | A9604 | >125 | 32 |
| S. faecalis | A20688 | 8 | 16 |
| S. aureus | A9537 | 0.5 | 2 |
| M. luteus | A9547 | 0.5 | 1 |
| S. aureus (Pen-Res) | A9606 | >250 | >250 |
| S. coli | A15119 | >250 | >250 |
| S. coli | A20341-1 | >250 | >250 |
| K. pneumoniae | A9664 | >250 | >250 |
| K. pneumoniae | A20468 | >250 | >250 |
| E. cloacae | A9659 | >250 | >250 |
| E. cloacae | A9656 | >250 | >250 |
| P. mirabilis | A9900 | >250 | >250 |
| P. vulgaris | A21559 | >250 | >250 |
| M. morganii | A15153 | >250 | >250 |
| P. rettgeri | A22424 | >250 | >250 |
| S. marcescens | A20019 | >250 | >250 |
| P. aeruginosa | A9843A | >250 | >250 |
| P. aeruginosa | A21213 | >250 | >250 |
| List. monocytogenes | A15121 | 32 | 32 |
| List. monocytogenes | A20025 | 32 | 63 |

4'-Deschlororebeccamycin was also tested against the transplanted mouse leukemia P-388 and the results are shown below in Table 6. The methodology used generally followed the protocols of the National Cancer Institute [Cancer Chemotherapy Rep. Part 3, 3, 1–103 (1972)]. The essential experimental details are given at the bottom of Table 6.

TABLE 6

Effect of 4'-Deschlororebeccamycin on P-388 Leukemia

| Material | Dose, IP mg/kg/inj | MST Days | MST % T/C | Average weight change, gm day 5 | Survivors day 10 |
| --- | --- | --- | --- | --- | --- |
| Rebeccamycin | 512 | 17.0 | 155 | −1.4 | 6/6 |
| | 256 | 15.0 | 136 | −0.3 | 6/6 |
| | 128 | 14.5 | 132 | 0.2 | 6/6 |
| | 64 | 15.0 | 136 | 0.3 | 6/6 |
| | 32 | 13.0 | 118 | −0.6 | 6/6 |
| | 16 | 15.0 | 136 | −0.8 | 6/6 |
| 4'-Deschlororebeccamycin | 512 | 15.5 | 141 | −1.0 | 4/4 |
| | 256 | 15.0 | 136 | −1.5 | 4/4 |
| | 128 | 17.5 | 159 | −0.6 | 4/4 |
| | 64 | 15.0 | 136 | −0.8 | 4/4 |
| | 32 | 15.5 | 141 | −0.8 | 4/4 |
| | 16 | 18.0 | 164 | −0.9 | 3/4 |
| Control | 0.5 ML | 11.0 | 100 | 0.6 | 10/10 |

Tumor inoculum: $10^6$ ascites cells, ip
Host: $CDF_1$ F mice
Treatment: Single injection on day 1 given i.p.
Evaluation: MST = median survival time
Effect: % T/C = (MST treated/MST control) × 100
Criteria: % T/C > 125 considered significant tumor inhibition
Control: Saline (0.5 ml) given once daily i.p. for 5 days As indicated by the antimicrobial and mouse tumor data provided above, 4'-deschlororebeccamycin is useful as an antibiotic and also as an antitumor agent for inhibition of mammalian malignant tumors such as P-388 leukemia.

The invention includes within its scope pharmaceutical compositions containing an effective antimicrobial or tumor-inhibiting amount of 4'-deschlororebeccamycin in combination with an inert pharmaceutically acceptable carrier or diluent. Such compositions may also contain other active antimicrobial or antitumor agents and may be made up in any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiological saline or some other sterile injectable medium immediately before use.

For use as an antimicrobial agent, the 4'-deschlororebeccamycin or pharmaceutical composition thereof is administered so that the concentration of active ingredient is greater than the minimum inhibitory concentration for the particular organism being treated. For use as an antitumor agent, optimal dosages and regimens of 4'-deschlororebeccamycin for a given mammalian host can be readily ascertained by those skilled in the art. It will, of course, be appreciated that the actual dose of 4'-deschlororebeccamycin used will vary according to the particular composition formulated, the mode of application and the particular situs, host and disease being treated. Many factors that modify the action of the drug will be taken into account including age, weight, sex, diet, time of administration, route of administration, rate of excretion, condition of the patient, drug combinations, reaction sensitivities and severity of the disease.

The following example is provided for illustrative purposes only and is not intended to limit the scope of the invention. Skellysolve B is a commercially available petroleum solvent (Skelly Oil Co.) comprising isomeric hexanes and having a boiling point of 60°–69° C. Dicalite is diatomaceous earth manufactured by Grefco, Inc. Unless otherwise indicated, all temperatures below are in degrees Centigrade.

EXAMPLE 1

Preparation of 4'-Deschlororebeccamycin

A. Fermentation

*Nocardia aerocolonigenes* strain C38,383-RK2 (ATCC 39243) was maintained and transferred in test tubes on agar slants of yeast-malt extract agar. This medium consists of 4.0 g glucose, 4.0 g yeast extract, 10 g malt extract and 20 g agar made up to one liter with distilled water. With each transfer the agar slant was incubated for seven days at 27° C. To prepare an inoculum for the production phase, the surface growth from the slant culture was transferred to a 500 ml Erlenmeyer flask containing 100 ml of sterile medium consisting of 30 g glucose, 10 g soy flour, 10 g cottonseed embryo meal and 3 g $CaCO_3$ made up to one liter with distilled water. This vegetative culture was incubated at 27° C. for 48 hours on a Gyrotory tier shaker (Model G53, New Brunswick Scientific Co., Inc.) set at 210 rev/min describing a circle with a 5.1 cm diameter. Four ml of vegetative culture was transferred to a 500 ml Erlenmeyer flask containing 100 ml of sterile production medium consisting of 60 g corn starch, 10 g glucose, 15 g linseed meal, 5.0 g autolyzed yeast, 1.0 g $FeSO_4.7H_2O$, 1.0 g $NH_4H_2PO_4$, 1.0 g $(NH_4)_2SO_4$ and 10 g $CaCO_3$ made up to one liter with distilled water. The production culture was incubated at 27° C. on a shaker such as used for the vegetative culture. The agitation rate was set at 250 rev/min. The fermentation was terminated at 168 hours.

B. Isolation

The fermentation broth obtained according to Example 1A is filtered using a diatomaceous earth filter aid (the filter aid is admixed with the broth and also used to form a mat). The filtrate is discarded and the mat extracted with tetrahydrofuran (THF) for 30–60 minutes using 0.1–0.2 volumes based on the original broth volume (the THF preferably contains 0.025% butylated hydroxytoluenes as preservative). The THF extract is filtered and the insolubles discarded. The filtrate is concentrated in vacuo until almost all the THF is removed. Inert filter aid is then admixed with the concentrate and the resulting mixture is filtered on a mat of inert filter aid. Air is sucked through the mat for four hours or more to dry the mat as much as possible.

The mat obtained as described above is then extracted for about 30 minutes with enough THF to get a good slurry. The extract is filtered and the mat discarded. The filtrate is concentrated by boiling at one atmosphere. Hot methanol is simultaneously added as the volume becomes low. After crystallization of yellow solids begins, the mixture is boiled gently until bumping becomes a problem. The reaction mixture is then allowed to cool and is chilled to 5°–8° C. The solid product is filtered, rinsed with cold methanol and dried. This material containing the desired 4'-deschlororebeccamycin is used in the following separation procedure.

C. Separation and Purification

Crude solids from Example 1B (336.3 g) were suspended and partially dissolved in 2.5 l of 2 parts chloroform: 1 part methanol and transferred to a 6 l round botton flask. Approximately 1 kg of filter aid (Dicalite) was mixed into the suspension. The mixture was diluted with approximately 1.5 l of Skellysolve B. The resultant slurry was concentrated to a powder in vacuo in a rotatory evaporator. This powder was slurried in 6 l of Skellysolve B and packed into a 12 cm o.d. × 90 cm flash chromatography column. A bed was formed with pressurized flow ($N_2$-5.7 psi). The packed column was eluted with pressurized flow with the following elutropic series: 9 liters of Skellysolve B (3 liters fresh + 6 liters packing solvent); 13 liters of toluene; 12 liters of methylene chloride; 12 liters of ethyl acetate; 18 liters of tetrahydrofuran; and 7 liters of methanol. The toluene eluant was evaporated to dryness in vacuo in a rotatory evaporator to yield 5.15 g of solid designated residue A.

A Glenco Series 3500 Universal LC column (2.67 cm i.d. × 75 cm) was packed with 80 g Woelm silica gel (0.063–0.200 mm) in chloroform. Residue A was dissolved in 40 ml of chloroform and pumped directly onto the column. Elution commenced with an initial isocratic rinse of 500 ml chloroform. Elution continued with a 4 l linear gradient of chloroform to 5 parts methanol in 95 parts chloroform collecting twenty 200 ml fractions. Fractions 13 to 16 were judged nearly homogeneous. These were pooled and evaporated to dryness to yield 663 mg of residue B.

The Glenco column (2.67 cm i.d. × 75 cm) was packed with Baker Bonded Phase Octadecyl silica gel (C-18) in methanol. The column was equilibrated with approximately 2.5 bed volumes of eluant: 3 parts acetonitrile, 3 parts methanol and 4 parts 0.1M ammonium acetate. Residue B in 3 ml of dimethylsulfoxide was drawn into the sample loop and pumped onto the column with eluant. Elution commenced while monitoring the eluant at 280 nm. After an initial 2 liter forerun, forty 50 ml fractions were collected. Based on the UV chromatogram, fractions 9 to 32 were pooled. The composite was extracted with 2 liters of chloroform. The lower phase was separated and concentrated to dryness in vacuo in a rotatory evaporator. The residue was partially dissolved in 50 ml of chloroform with sonication. The suspension was added to 1 liter of Skellysolve B with rapid stirring. The resultant precipitate was collected by filtration to yield 606 mg of 4'-deschlororebeccamycin.

Further details of the above isolation procedure are set forth below:

Analytical HPLC:

The following components were used to construct an analytical HPLC system: Waters Associates Model 6000A Solvent Delivery System pump; Varian Varichrom Model VUV-10 uv/vis Detector set at 254 nm 0.1 O.D.; Fisher Recordal Series 5000 Recorder; Waters Associates Model U6K injector; Altex Spherisorb ODS (10μ) column (4.6 mm i.d. × 25 cm). The components were connected with 316 stainless steel tubing (1.6 mm o.d.–0.23 mm i.d.). The eluant of 4 parts acetonitrile, 3 parts methanol, and 3 parts 0.1M ammonium acetate was pumped at 2 ml/min for all analysis. Occasionally, a Hewlett Packard 1040A HPLC Detector System was substituted for the Varian Varichrom VUV-10 Detector.

Thin Layer Chromatography (TLC):

TLC was carried out on Analtech precoated Silica Gel GHLF plates (2.5 cm × 10 cm 0.25 mm thick layers). The plates were developed in glass cylinders (6.4 cm diameter by 15 cm high) purchased from Whatman, Inc. The tanks were charged with 10 ml of 5 parts methanol-95 parts chloroform and allowed to equilibrate prior to introducing the plate. The developed, air dried plates were visualized with 254 nm and 366 nm ultraviolet light using either a Chromato-VUE model CC-20 light box (Ultra-Violet Products Inc.) or a model UVSL-58 hand held mineral light lamp (Ultra-Violet Products Inc.).

Preparative HPLC:

The following components were used to construct a medium pressure liquid chromatography system: Fluid Metering, Inc. Model RP-SY 2CSC FMI Lab Pump; Fluid Metering Inc. Model PD-60-LF FMI Pulse Dampener; a 15 ml sample loop constructed of polypropylene tubing (3.0 mm o.d. $\times$ 1.5 mm i.d.) wrapped around a cardboard tube (8.65 cm o.d.); Glenco Series 3500 Universal LC column (2.67 cm i.d. $\times$ 75 cm); Instrumentation Specialties Co. Model UA-5 Absorbance/Fluorescence Monitor with a Type 6 optical unit; Instrumentation Specialties Co. Model 590 Flow Interrupter Value; and an Instrumentation Specialties Co. Model 328 Fraction Collector. The components were connected with polypropylene and Teflon tubing (3.0 mm o.d. $\times$ 1.5 mm i.d.) and Glenco multifit connectors and valves in the order listed.

The Glenco series 3500 Universal LC column was slurry packed with the defined adsorbent in the designated solvent using standard techniques. The void between the settled bed and tube top was filled with standard Ottawa sand. Eluant was pumped at a maximum rate which would not exceed 60 psi back pressure (approximately 20 ml/min).

Gradient Elution:

A Glenco gradient elution apparatus consisting of two chambers of equal diameter, height and volume connected in tandem with a Teflon valve was used for gradient elutions. One chamber served as a mixing chamber and one as a static reservoir. The less polar solvent, chloroform, was initially held in the mixing chamber. The more polar solvent 5 parts methanol in 95 parts chloroform, was held in the static chamber. Teflon coated magnetic stirring bars (1.0 $\times$ 3.7 cm) were placed in both chambers and driven by Thomas Model 15 Magne-matic stirrers. Eluant was pumped from the mixing chamber to the medium pressure hplc system through polypropylene tubing (1.5 mm i.d. $\times$ 3.0 mm o.d.). As eluant was removed from the mixing chamber, the solvent in the static reservoir was allowed to freely replace it, thus creating a linear gradient of eluant.

We claim:

1. a process for producing 4'-deschlororebeccamycin having the formula

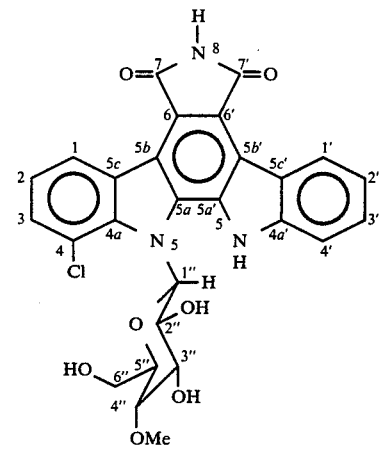

which comprises cultivating a *Nocardia aerocolonigenes* ATCC 39243 or a 4'-deschlororebeccamycin-producing mutant thereof in an aqueous nutrient medium containing assimilable sources of carbon and nitrogen under submerged aerobic conditions until a substantial amount of 4'-deschlororebeccamycin is produced by said organism in said culture medium and then isolating said 4'-deschlororebeccamycin from the culture medium in a substantially pure form.

* * * * *